Aug. 13, 1957 J. M. ROXBURGH Plant Pat. 1,632
PEACH TREE
Filed Nov. 20, 1956
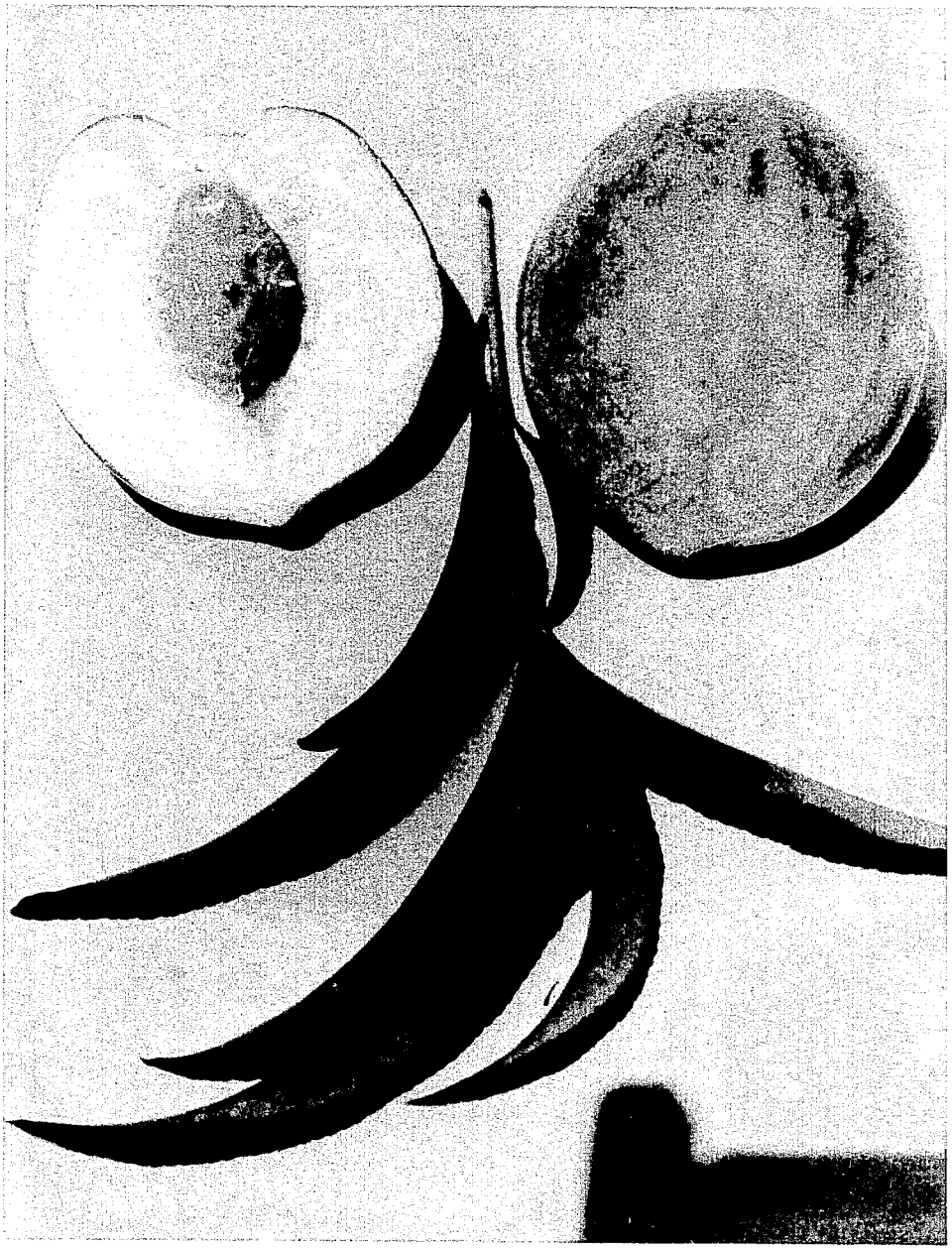
INVENTOR
J. M. Roxburgh
BY Robb & Robb
ATTORNEYS United States Patent Office Plant Pat. 1,632
Patented Aug. 13, 1957

1,632

PEACH TREE

John M. Roxburgh, Simcoe, Ontario, Canada, assignor to Stark Bro's Nurseries and Orchards Company, Louisiana, Mo., a corporation of Missouri Application November 20, 1956, Serial No. 623,513

1 Claim. (Cl. 47—62)

The present invention relates to a new and distinct variety of peach tree which was discovered by me as a bud sport of the variety known as "Red Haven" (unpatented), the discovery having been made in my cultivated orchard located in Woodhouse Township, Norfolk County, Ontario, Canada.

While picking other early peach varieties in a part of my orchard referred to above, my attention was attracted to an unusually early coloring of the fruit on a limb of a "Red Haven" peach tree, and I thereupon kept this limb under close observation. Continued observation and subsequent tests and asexual reproduction of the limb sport aforesaid fully established and confirmed that the early coloring of the fruit thereof was fixed and came true to form by asexual reproduction.

In addition to the early coloring habit of the fruit as aforesaid, the tests and observations further established the following characteristics of the new sport, which, when taken together, represent a new and improved combination of features:

(1) A heavy bearing habit, with the fruit generally resembling that of "Red Haven" in size, color and flavor;

(2) An early fruit-ripening habit approximately 10 days before "Red Haven";

(3) The high quality of the fruit;

(4) The good red color of the fruit and its habit of coloring at least a week before the fruit attains full size;

(5) The moderately firm flesh of the fruit;

(6) A heavy red mottling throughout the flesh of the fruit; and (7) A very slow browning of the flesh when cut.

Asexual reproduction of my new variety by budding, as performed in my orchard in Ontario, Canada, and also as performed in Pike County, Missouri, U. S. A., shows that the foregoing characteristics come true to form and are established and transmissible through succeeding propagations, and definitely differentiate the new sport from its parent, as well as from all other peach varieties of which I am aware.

The accompanying drawing shows typical specimens of the fruit and foliage of the new variety, with the fruit shown in both section and elevation, all as depicted in color as nearly true as it is reasonably possible to make the same in a color illustration of this character.

The following is a detailed description of the new variety, with color terminology in accordance with Ridgway's Color Standards and Nomenclature (hereinafter abbreviated as "Ridgway"), and with the Horticultural Color Guide (hereinafter abbreviated as "HCG"), except where general color terms of ordinary dictionary significance are obvious:

Observations made from specimens grown in Pike County, Missouri, U. S. A.

Dates of first and last pickings—about July 16th and July 24th, respectively.

Tree: Medium size; medium vigorous; open; spreading; vase-formed; hardy; productive; regular bearer.

*Trunk.*—Medium stockiness.

*Branches.*—smooth. Color—Tawny Olive, Plate XXXIX, color No. 17", Tone *i* (Ridgway). Lenticels—medium number; medium size.

*Leaves.*—Medium size; length about 6 inches; width about 1⅝ inches; ovate; acutely pointed; medium thickness; smooth. Color—Parsley Green, Plate 00962/1, page 193, vol. II (HCG). Margin—glandular; finely serrate. Petiole—medium length; medium thickness. Glands—average 2 or 3 on petiole, and 2 or 3 on leaf; alternate; medium size; mixed (some globose, but most reniform); free.

Flowers:

*Dates of first and full bloom.*—About April 10 and about April 16; considered as medium early.

*Size.*—Medium.

*Color.*—Spirea Red, Plate 025/2, page 112, vol. II (HCG), shading to white at base and center of some petals.

Fruit:

*Maturity when described.*—Hard-ripe. Date—July 17.

*Size.*—Uniform; medium. Axial diameter—about 2⅝ inches. Transverse diameter in suture plane—about 2⅝ inches. Diameter at right angles to suture plane—about 2⅝ inches.

*Form.*—Uniform; symmetrical; globose; sides unequal.

*Suture.*—Shallow; extends from base to apex; has a slight marked depression beyond pistil point.

*Ventral surface.*—Rounded; strongly lipped toward base; lips equal.

*Cavity.*—Abrupt; elongated; with suture showing on both sides. Depth—about 9/16 inch. Breadth—About ⅞ inch. Markings—none.

*Base.*—Oblique; rounded.

*Apex.*—Short; oblique.

*Stem.*—About ⅙ inch long; stout; glabrous; medium adherence to stone.

*Skin.*—Medium thickness; tough; free; no tendency to break in wet or dry seasons. Color—Highly blushed with Carmine, Plate 21/1, page 21, vol. I (HCG), with stripings and markings of Rose Opal, Plate 022, page 110, vol. II (HCG). Down—moderate; medium length; does not roll up when rubbed.

*Flesh.*—Color—Lemon Yellow, plate 4/2, page 4, vol. I (HCG), mottled throughout with Carmine, Plate 21/1, page 21, vol. I (HCG).

*Surface of pit cavity.*—Color—Lemon Yellow, Plate 4/2, page 4, vol I (HCG), with fibers of Carmine, Plate 21/3, page 21, vol. I (HCG).

*Amygdalin.*—Wanting.

*Juice.*—Abundant; rich.

*Texture.*—Meaty.

*Fibers.*—Few; fine; tender.

*Ripens.*—Fairly evenly.

*Flavor.*—Mild.

*Aroma.*—Distinct.

*Eating Quality.*—Good.

Stone: Semi-free; adheres to flesh along dorsal edges.

*Fibers.*—Short; retails short fiber-like threads along ridges.

*Size.*—Medium. Length—about 1½ inches. Thickness—about ¾ inch.
*Form.*—Oval; cuneate toward base and apex.
*Base.*—Oblique; narrow; oval.
*Apex.*—Acute.
*Sides.*—Equal; curved on right and left sides.
*Surface.*—Irregularly furrowed throughout; pitted throughout.
*Ridges.*—Ragged from base to apex.
*Pits.*—Circular.
*Ventral edge.*—Thick; with wing toward base.
*Dorsal edge.*—Full; narrow groove toward base; ridges in either side continuous.
Use: Local market; dessert.
Keeping quality: From medium to good.
Shipping quality: From medium to good.

I claim:

A new and distinct variety of peach tree of the semi-freestone type, substantially as herein shown and described, characterized particularly as to novelty by its heavy bearing habit, with fruit generally resembling that of "Red Haven" (unpatented) in size, color and flavor, its early-ripening habit, the high quality of its fruit, the good red color of the fruit and its habit of coloring at least a week before the fruit attains full size, the moderately firm flesh of the fruit, the heavy red mottling throughout the flesh of the fruit, and the very slow browning habit of the flesh of the fruit when cut.

No references cited.